US011185223B2

(12) United States Patent
Ohlendorf et al.

(10) Patent No.: US 11,185,223 B2
(45) Date of Patent: Nov. 30, 2021

(54) DETERMINATION OF A CHANGE IN A REFRACTIVE ERROR OF AN EYE

(71) Applicant: Carl Zeiss Vision International GmbH, Aalen (DE)

(72) Inventors: Arne Ohlendorf, Tübingen (DE); Katharina Breher, Tübingen (DE); Siegfried Wahl, Donzdorf (DE)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 17/183,573

(22) Filed: Feb. 24, 2021

(65) Prior Publication Data

US 2021/0177255 A1    Jun. 17, 2021

Related U.S. Application Data

(63) Continuation of application No. PCT/EP2020/069566, filed on Jul. 10, 2020.

(30) Foreign Application Priority Data

Jul. 11, 2019    (EP) .................................... 19185709

(51) Int. Cl.
*A61B 3/103*    (2006.01)
*A61B 3/10*    (2006.01)
(Continued)

(52) U.S. Cl.
CPC ............ *A61B 3/103* (2013.01); *A61B 3/0025* (2013.01); *A61B 3/102* (2013.01); *A61B 3/1005* (2013.01);
(Continued)

(58) Field of Classification Search
CPC .. A61K 2300/00; A61K 31/46; A61K 31/522; A61K 9/0048; A61B 3/102;
(Continued)

(56) References Cited

U.S. PATENT DOCUMENTS

2012/0150029 A1* 6/2012 Debuc ....................... G06T 7/12
                                                            600/425
2017/0172405 A1   6/2017 Torii et al.
(Continued)

FOREIGN PATENT DOCUMENTS

WO    2015188279 A1    12/2015
WO    2018165697 A1    9/2018

OTHER PUBLICATIONS

Written Opinion issued in PCT/EP2020/069566, to which this application claims priority, dated Oct. 26, 2020, and English-language translation thereof.
(Continued)

*Primary Examiner* — Baisakhi Roy
(74) *Attorney, Agent, or Firm* — Thrive IP®; Georg Hasselmann (57) ABSTRACT

A method, an apparatus, and a computer program for determining a refractive error of an eye of a user are provided. The method for determining the refractive error of the eye of the user, wherein the eye of the user has a choroid, includes:
  ascertaining at least one value for a layer thickness of the choroid of the eye of the user over at least one region of the choroid; and
  determining a value for the change in the refractive error of the eye only from at least two values for the layer thickness of the choroid which were each ascertained at different times for the at least one region of the choroid, wherein the at least one region is selected from a nasal perifoveal region or a nasal parafoveal region.

18 Claims, 3 Drawing Sheets

(51) Int. Cl.
  *A61B 3/14* (2006.01)
  *A61B 5/00* (2006.01)
  *A61B 8/10* (2006.01)
  *A61B 3/00* (2006.01)
  *G06T 7/00* (2017.01)
  *G16H 50/30* (2018.01)
  *G16H 30/40* (2018.01)

(52) U.S. Cl.
  CPC .............. *A61B 3/14* (2013.01); *A61B 5/0095* (2013.01); *A61B 8/10* (2013.01); *G06T 7/0016* (2013.01); *G16H 30/40* (2018.01); *G16H 50/30* (2018.01); *G06T 2207/10101* (2013.01); *G06T 2207/30041* (2013.01)

(58) Field of Classification Search
  CPC ..... A61B 3/0025; A61B 3/032; A61B 3/0285; A61B 3/0041; A61B 3/103; A61B 3/14
  See application file for complete search history.

(56) References Cited

U.S. PATENT DOCUMENTS

| | | | |
|---|---|---|---|
| 2019/0033619 A1* | 1/2019 | Neitz | G02C 7/022 |
| 2019/0142778 A1* | 5/2019 | McFadden | A61P 27/10 514/561 |
| 2019/0282828 A1* | 9/2019 | Rucker | A61N 5/0613 |
| 2020/0075155 A1* | 3/2020 | Huang | G06T 7/10 |
| 2020/0345633 A1* | 11/2020 | Coroneo | A61K 31/46 |

OTHER PUBLICATIONS

International Search Report issued in PCT/EP2020/069566, to which this application claims priority, dated Oct. 26, 2020, and English-language translation thereof.

Industrial Norm "Ophthalmic optics—Spectacle lenses—Vocabulary (ISO 13666:2012)," German and English version EN ISO 13666:2012, Oct. 2013.

Cirrus HD-OCT User Handbook, "Beschreibung der in CIRRUS HD-OCT verwendeten Makula-Scan-Parameter [Description of the macula scan parameters used in CIRRUS HD-OCT]," 2660021164328 Rev. A Oct. 2016, Appendix A-7, Oct. 2016. Relevance is found at least in paragraph [0032] of the specification.

Wallman "Moving the Retina: Choroidal Modulation of Refractive State," Vision Res. 35(1), pp. 37 to 50, 1995.

Trolio et al. "Choroidal Thickness Changes during Altered Eye Growth and Refractive State in a Primate," Investigative Ophthalmology & Visual Science 41 (6), pp. 1249 to 1258, 2000.

Read et al. "Human Optical Axial Length and Defocus," Investigative Ophthalmology & Visual Science 51 (12), pp. 6262 to 6269, 2010.

Flores-Moreno et al. "The Relationship Between Axial Length and Choroidal Thickness in Eyes With High Myopia," Am. J. Ophthalmology 155 (2), pp. 314 to 319, 2012.

Ho et al: "Chorodial Thickness Measurement in Myopic Eyes by Enhanced Depth Optical Coherence Tomography," Ophthamology, vol. 120, No. 9, pp. 1909 to 1914, Sep. 1, 2013.

Chiang et al. "Effect of retinal image defocus on the thickness of the human choroid," Ophthalmic Physiol. Opt, 35, pp. 405 to 413. doi: 10.1111/ opo.12218, 2015.

Wang et al. "Optical Defocus Rapidly Changes Choroidal Thickness in Schoolchildren," PLoS One 11(8): e0161535, doi: 10.1371/journal. pone. 0161535, pp. 1 to 12, Aug. 18, 2016.

International Search Report issued in PCT/EP2019/069422, to which this application claims priority, dated Oct. 26, 2020, and English-language translation thereof.

\* cited by examiner

DETERMINATION OF A CHANGE IN A REFRACTIVE ERROR OF AN EYE

CROSS REFERENCE TO RELATED APPLICATIONS

This application is a continuation application of international patent application PCT/EP2020/069566, filed Jul. 10, 2020, designating the United States and claiming priority from European patent application 19 185 709.3, filed Jul. 11, 2019, and the entire content of both applications is incorporated herein by reference.

TECHNICAL FIELD

The present disclosure relates to a method, an apparatus, and a computer program for determining a change in a refractive error of an eye of a user.

BACKGROUND

The related art has disclosed methods for determining refractive errors of an eye of a user. Here, the term "refraction" denotes a refraction of light in the eye of the user which is experienced by a light beam incident in the interior of the eye through the pupil. By having available a number of spectacle lenses with known properties and by guiding the user through a questionnaire process, it is possible to subjectively determine the defocusing of the eye of the user and to determine which, e.g., spherocylindrical configuration of the spectacle lens leads to a substantial compensation of the refractive error of the eye and hence to an image quality for the user that is as optimal as possible. Defocusing of the eye of the user can lead to a refractive error (ametropia) of the user, in particular to nearsightedness (myopia) or farsightedness (hyperopia). An increased prevalence of myopia, particularly in children and adolescents, can be observed in Asiatic countries in particular, with the myopia being caused in approximately 80% of cases by an increased eye length growth. As a rule of thumb, a lengthening of the eyeball of approximately 1 mm leads to a refractive error of approximately 3 dpt.

Furthermore, capturing the refraction of the eye by measurement with and without a cycloplegic agent, i.e., a pharmaceutical for reducing the ability of the eye to accommodate, for the purposes of determining a change in the refractive error of the eye is known. This can be carried out, in particular, for monitoring the progress of a refractive error or for observing an effectiveness of approaches for reducing the progression of the refractive error. Alternatively, it is possible to capture an axial length of the eye, in particular from the anterior surface or posterior surface of the cornea to the retinal pigment epithelium of the retina, over a relatively long period of time by means of optical laser biometry, for example, and it is possible to observe this growth over this period of time. To this end, progress can be monitored over the period of time of one to three years, with at least two measurements being carried out each year as a rule. However, other intervals are also possible, for example a measurement at least every week, month or year. In this case, a statement about the individual progression or the effectiveness of a selected approach for reducing the progression is only available after this period of time has expired.

Further, a relationship is known to exist between the layer thickness of the choroid of the eye and the axial length of the latter. Moreover, the choroid is known to be able to react to externally induced dioptric stimuli by way of a change in thickness, and the time resolution of such a reaction is known to be in the range of minutes. By way of example, data ascertained by means of optical coherence tomography (OCT) can be used to determine the change in the layer thickness of the choroid. Further options of optical intervention for reducing the progression of myopia are based on dioptric theories, for example an under-accommodation theory or a peripheral defocus theory, wherein OCT measurements, more particularly spectral domain OCT (SD-OCD) and swept source OCT, can be used to determine the influence of an intervention option on the choroidal thickness. If the change in the choroidal thickness is ascertained by means of OCT, it is possible to make a statement about the thinning or thickening of the choroid already after a number of minutes or hours.

However, the repeatability of measurements of the layer thickness of the choroid is generally insufficient to be able to actually verify the size of the effect, described in the literature, of approximately 10 μm to 30 μm or up to 50 μm in the case of primates or 260 μm in the case of chickens. References to such measurements can be found in D. Wang, R. K. M. Chun, M. Liu, R. P. K. Lee, Y. Sun, T. Zhang, C. Lam, Q. Liu and C. H. Tol, *Optical Defocus Rapidly Changes Choroidal Thickness in Schoolchildren*, PLoS ONE 11(8): e0161535, doi: 10.1371/journal.pone.0161535, 2016; S. A. Read, M. J. Collins, and B. P. Sander, *Human Optical Axial Length and Defocus*, Investigative Ophthalmology & Visual Science 51(12), pp. 6262-69, 2010; S. T-H. Chiang, J. R. Phillips and S. Backhouse, *Effect of retinal image defocus on the thickness of the human choroid*, Ophthalmic Physiol. Opt, 35: 405-413. doi: 10.1111/opo.12218, 2015; D. Troilo, D. L. Nickla and C. F. Wildsoet, *Choroidal Thickness Changes during Altered Eye Growth and Refractive State in a Primate*, Investigative Ophthalmology & Visual Science 41 (6), pp. 1249-58, 2000; and J. Wallman, C. Wildsoet, A. Xu, M. D. Gottlieb, D. L. Nickla, L. Marran, W. Krebs, A. M. Christensen, *Moving the Retina: Choroidal Modulation of Refractive State*, Vision Res. 35(1), pp. 37-50, 1995.

WO 2018/165697 A1 discloses apparatuses and methods for implementing an ophthalmological lens design. Following the implementation, the influence of the ophthalmological lens design can be measured by means of an ocular biometric apparatus. The influence of the ophthalmological lens design on the layer thickness of the choroid was captured, in particular using a combination of an adaptive optical apparatus and the ocular biometric apparatus. To this end, measurements were taken at different positions on the retina including the fovea and at the retinal periphery.

US 2019/0033619 A1 discloses a method for monitoring and inhibiting an advance of near-sightedness (myopia) in a person, comprising: measuring a change in the layer thickness of the choroid over a period of time, in particular by means of optical coherence tomography (OCT); and providing ophthalmological lenses, in particular in the form of spectacle lenses or contact lenses, for reducing a contrast in peripheral vision in comparison with the contrast for vision along the axis of the eye. The respectively obtained experimental results are presented here as a function of the position on the retina.

Flores-Moreno Ignacio et al., *The Relationship Between Axial Length and Choroidal Thickness in Eyes With High Myopia*, Am. J. Ophthalmology 155 (2), 2012, pp. 314-319, disclose examinations of the layer thickness of the choroid in highly myopic eyes and the correlation thereof with the axial length of the eye, the age of the person and the spherical equivalent of the refractive error. The layer thickness of the choroid was measured from the outer end of the retinal pigment epithelium to the transition to the sclera in intervals of 500 µm to 2500 µm nasally and temporally in relation to the fovea.

SUMMARY

Proceeding, in particular, from the disclosure in WO 2018/165697 A1 or US 2019/033619 A1, the object of the present disclosure is directed to providing a method, an apparatus and a computer program for determining a change in a refractive error of an eye of a user, which at least partly overcome the listed disadvantages and limitations of the related art.

In particular, the present method, the apparatus and the computer program should allow a reliable determination of the change in the refractive error of the eye, typically for classifying an advance of a refractive error or for a statement about the success of an intervention for reducing the advance of the refractive error, by measuring the layer thickness of the choroid with a high repeatability of the measurement results.

This object is achieved by a method, a computer program and an apparatus for determining a change in a refractive error of an eye of a user by ascertaining at least one value for a layer thickness of the choroid of the eye of the user. Typical configurations, which can be realized individually or in combination, are presented in detail below.

Hereinafter the terms "exhibit," "have," "comprise," or "include" or any grammatical deviations therefrom are used in a non-exclusive way. Accordingly, these terms can refer either to situations in which, besides the feature introduced by these terms, no further features are present, or to situations in which one or more further features are present. For example, the expression "A exhibits B," "A has B," "A comprises B," or "A includes B" can refer both to the situation in which no further element aside from B is provided in A, that is to say to a situation in which A consists exclusively of B, and to the situation in which, in addition to B, one or more further elements are provided in A, for example element C, elements C and D, or even further elements.

By way of example, the refractive error of an eye can typically be largely compensated by a spectacle lens with spherical correction and/or astigmatic correction and correction of the axis and optionally by means of correction by a prism with a base. The aforementioned corrections can typically largely compensate the near and/or distance refractive error of an eye.

The present disclosure understands "refractive error" to mean all defects of an eye that can be compensated by means of spherical correction and/or astigmatic correction and the correction of the axis and optionally by means of the correction by a prism with a base, in each case for the distance. Here, the refractive error can comprise one, some or all of the defects listed above.

In a first aspect, the present disclosure relates to a method for determining a change in a refractive error of an eye of a user. The method comprises the following steps a) and b), typically in the specified order, wherein the method steps can be carried out simultaneously in full or in part. Furthermore, steps of this method can be carried out repeatedly, in particular more than once. The method might also comprise further steps in addition to the aforementioned method steps, independently of whether or not the further steps are mentioned in the present description. In particular, this can include a step which comprises a capture of a layer thickness of the choroid of the eye of the user by measurement.

The method for determining a change in a refractive error of an eye of a user, the eye of the user having a choroid, comprises the steps of:
  a) ascertaining at least one value for a layer thickness of the choroid of the eye of the user over at least one region of the choroid; and
  b) determining a value for the change in the refractive error of the eye only from at least two values for the layer thickness of the choroid which were each captured at different times for the at least one region of the choroid, wherein the at least one region of the choroid is selected from a nasal perifoveal region or a nasal parafoveal region of the choroid.

The change in the refractive error determinable by the method typically comprises the correction for the distance, particularly typically the spherical and astigmatic correction and the correction of the axis, respectively for the distance, very typically the spherical correction for the distance. Alternatively, it is also possible to determine the change in the spherical equivalent.

As described in more detail below, the present method for determining the change in the refractive error of the eye of a user facilitates, in particular, a classification of an advance of the refractive error or a statement about the success of an intervention for reducing the advance of the refractive error by virtue of implementing a measurement of the layer thickness of the choroid at different times, wherein the measurement results obtained thereby—in contrast to the methods known from the related art—have a high repeatability. Hence, using the present method, it is already possible to determine a change in the refractive error of an eye with a high significance after only a few minutes.

According to step a) of the present disclosure, at least one value for a layer thickness of the choroid of the eye of the user is ascertained over at least one region of the choroid. Here, the terms "choroid" and "choroidea" denote an intermediate layer arranged, between the sclera and the retina, in particular between the sclera and the retinal pigment epithelium, on the side of the eye distant from the entrance of light. What emerges from this type of arrangement of the choroid in the eye is that the layer thickness of the choroid is delimited by the respectively adjoining sclera and retina, in particular the sclera and the retinal pigment epithelium. The term "layer thickness of the choroid" within the scope of the present disclosure denotes a distance between the sclera and the retina, with the distance being determined substantially perpendicular to a direction of extent of the choroid. Here, the extent of the choroid can exceed the layer thickness of the choroid by at least a factor of 10, typically by at least a factor of 20, particularly typically by at least a factor of 50. In respect of further details relating to the arrangement of the choroid and the associated layer thickness, reference is made to the description of the exemplary embodiments below and to the figures.

In principle, ascertaining the at least one value for the layer thickness of the choroid as per step a) of the present method can be preceded by the capture of the layer thickness of the choroid, which can be implemented using any procedure and using any desired apparatus, in particular a measuring device as described in more detail below, which is configured to capture the layer thickness of the choroid. Here, the term "capture" relates to a recording of at least one variable captured by measurement, from which the layer thickness can be derived. In this case, capturing the layer thickness of the choroid of the eye can typically comprise a generation of a spatially resolved recording of the eye, wherein the recording at least contains a region of the choroid and, typically, a region of the sclera and the retina, in particular the retinal pigment epithelium, respectively adjoining the region of the choroid. However, different ways of capturing the layer thickness of the choroid are possible.

In a typical configuration, a method selected from an optical method, an acoustic method or a photoacoustic method can be used to capture the layer thickness of the choroid of the eye, wherein, in accordance with the respectively selected method, use can be made of an optical measuring device, an acoustic measuring device or a photoacoustic measuring device. However, in principle, further methods are possible.

In a particularly typical configuration, the layer thickness of the choroid can be captured using an optical method. The term "optical method" in this case denotes a procedure in which light, typically light from the visible or infrared spectral range, impinges on the choroid of the eye, in particular, whereupon a reflection of the light at the choroid following this application of light allows conclusions to be drawn about a characteristic of the choroid, in particular the layer thickness of the choroid. In contrast thereto, "acoustic method" and "photoacoustic method" each denote a procedure in which the choroid is impinged by acoustic waves, typically ultrasound, with the capture by measurement likewise being implemented in acoustic or optical fashion.

In a particularly typical configuration, the optical method can be selected from a method for optical coherence tomography. Here, the term "optical coherence tomography," also abbreviated "OCT," denotes an imaging method for generating a two-dimensional or three-dimensional recording of biological tissue, in particular of the choroid of the eye and layers adjoining the latter, wherein a resolution in the micrometer range can typically be obtained. To generate the desired recording, light with a temporally short coherence length from a radiation source is split into two parts in a beam splitter, wherein a first part of the light impinges on the tissue along an optical axis, wherein a second part of the light is guided over a reference path, and wherein the light reflected by the tissue is made to interfere with the reference light guided over the reference path in order to generate an interference signal. From the interference signal generated thus, it is possible initially to only distinguish structures in the tissue along the optical axis; however, the desired two- or three-dimensional recording of the tissue or a section thereof can be generated by way of a lateral scanning by means of a change in the optical axis over the tissue.

Typically, the optical coherence tomography method can be selected from a Fourier domain OCT or a time domain OCT, with the Fourier domain OCT, in particular spectral domain OCT or swept source OCT, being particularly typical. The term "time domain OCT" denotes a procedure in which a length of the reference path is altered and an intensity of the interference is continuously captured in the process, with a change in the frequency spectrum of the interference remaining unconsidered. By contrast, "Fourier domain OCT" denotes a procedure in which the change in components of the frequency spectrum of the interference is taken into account. If the change in the frequency spectrum of the interference is simultaneously excited and captured by means of a broadband radiation source, this procedure is referred to as "spectral domain OCT." By contrast, in "swept source OCT," the components of the frequency spectrum are temporally successively excited and captured, in particular by successive tuning of the frequency excitation of the radiation source.

In an alternative configuration, the optical method can be selected from an adaptive optical method. The term "adaptive optical method" in this case denotes an optical method in which an imaging optical system, which comprises a beam path with imaging properties, is configured to compensate optical changes occurring in the beam path by way of a change in the imaging properties, wherein it is possible to draw conclusions about optical changes in the beam path from the change in the imaging properties. As a result, it is possible according to the disclosure to deduce a layer thickness of the choroid if the choroid is integrated into the optical system in such a way that a change in the layer thickness of the choroid alters the imaging properties of the optical system. Typically, the adaptive optical method can be selected from a method for determining an optical transmission or a method for determining an optical reflectivity such that a change in the optical transmission or reflectivity of the choroid, typically by means of so-called "fundus reflectivity," alters the imaging properties of the optical system and thus facilitates the desired capture of the layer thickness of the choroid. However, other types of adaptive optical methods and devices are conceivable.

According to step a), furthermore, an ascertainment of the at least one value for the layer thickness of the choroid is effected. In this case, the term "ascertainment" relates to the determination of a value for the layer thickness of the choroid from at least one variable captured by measurement, from which the layer thickness can be derived. Here, the ascertainment of the value for the layer thickness of the choroid can typically comprise determining the value for the layer thickness from a spatially resolved recording of the eye, particularly if an optical coherence tomography method is selected, wherein the recording includes at least a region of the choroid and, typically, a respective adjoining region of the sclera and the retina, in particular the retinal pigment epithelium. However, other ways of ascertaining the layer thickness of the choroid are possible, particularly if an above-described adaptive optical method is used to capture the layer thickness.

According to step a), the at least one of value for the layer thickness of the choroid is ascertained over at least one region of the choroid. The at least one region of the choroid in this case denotes a section of the choroid which, as explained in more detail below, can typically be selected in relation to a point of the retina adjoining the section. In this case, a value for an average layer thickness of the choroid can typically be ascertained over the at least one region of the choroid. Here, the "average layer thickness" denotes a mean, typically an arithmetic or geometric mean, a median or any other suitable representative value for the layer thickness of the choroid over the at least one region. The "average layer thickness" particularly typically denotes an arithmetic mean. However, a different value for the layer thickness of the choroid over the at least one region of the choroid is conceivable.

According to step b), there is a determination of the value for the change in the refractive error of the eye of the user, typically in an evaluation device described in more detail below, by preference following the ascertainment of the at least one value for the layer thickness of the choroid over the at least one region of the choroid in accordance with step a). According to the present disclosure, only at least two values for the layer thickness of the choroid are used to this end, the values each being ascertained at different times for the at least one region of the choroid according to step a). Typically, for this purpose, a first value for the layer thickness of the choroid is ascertained at a first time and a second value for the layer thickness of the choroid is ascertained at a second time, wherein the desired value for the change in the refractive error of the eye of the user can be ascertained from relating the two values, i.e., the first value and the second value. To this end, it is possible to estimate a value for a lengthening of the eyeball of the user, for example from the change in the layer thickness which can be ascertained from a difference between the first value for the layer thickness of the choroid and the second value for the layer thickness of the choroid. Using the rule of thumb set forth at the outset, according to which a lengthening of the eyeball of approximately 1 mm leads to a refractive error of approximately 3 dpt, it is consequently possible to deduce the change in the refractive error of the eye of the user. However, other ways of determining the value for the change in the refractive error of the eye of the user are possible.

According to the present disclosure, the at least one region of the choroid is selected from a nasal perifoveal region or a nasal parafoveal region of the choroid according to step b) for determining the value for the change in the refractive error, with the nasal perifoveal region of the choroid being particularly typical. In this case, the at least one region of the choroid denotes a section of the choroid, in particular in relation to a point of the retina adjacent to the section, typically in relation to the fovea which comprises a depression in the retina of the eye situated in the center of the macula lutea, which is considered to be the region of sharpest vision in humans and mammals.

In a particularly typical configuration, an area of the retina and hence of the choroid adjacent thereto can be split into a subfoveal region, parafoveal regions or inner regions surrounding the subfoveal region and perifoveal regions or outer regions surrounding the parafoveal regions. Here, the subfoveal region can typically have a diameter ranging from 0.5 mm to 1.5 mm, typically 1 mm, corresponding to an angle of 3.33°, while the parafoveal regions can extend from touching the latter up to an inner diameter and the perifoveal regions can extend from touching the latter up to an outer diameter, wherein the inner diameter is typically selected from a value from 2 mm to 4.5 mm, typically 2.5 mm to 4 mm, in particular 3 mm, corresponding to an angle of 10°, and the outer diameter is selected from a value of 5 mm to 20 mm, typically 5 mm to 12 mm, in particular 6 mm, corresponding to an angle of 20°. However, other values of the diameters specified here are conceivable.

As already mentioned, the value for the change in the refractive error as per step b) is determined according to the disclosure by using the at least two values for the layer thickness of the choroid, which are ascertained for a nasal perifoveal region or a nasal parafoveal region of the choroid. As emerges from the exemplary embodiments below and the figures, an outer nasal region and/or an outer temporal region of the retina, in particular the regions denoted "7" (right eye) and "9" (left eye) as per the so-called "ETDRS grid" of the retina, are particularly typically suitable to this end. The ETDRS grid of the retina relates to a so-called "Early Treatment Diabetic Retinopathy Study (ETDRS) Grid", as can be found, for example, in the CIRRUS HD-OCT user handbook, 2660021164328 Rev. A 2016-10, Appendix A-7. Therein, the retina is divided into regions from 1 to 9 in relation to the relative position of the fovea.

While known methods for determining the change in the layer thickness of the choroid evaluate possible changes in the layer thickness of the choroid predominantly in the subfoveal region of the retina in particular, it was surprisingly possible to show by experiment (see table 1 below) that the reproducibility of the evaluation is significantly better in the nasal perifoveal regions, i.e., in regions 7 and 9 in the ETDRS grid, and in the nasal parafoveal region, i.e., in region 3 for the right eye and in region 5 for the left eye in the ETDRS grid, but particularly in the nasal perifoveal region, i.e., in region 7 for the right eye and in region 9 for the left eye, than in the subfoveal region of the retina and in the other regions of the choroid. Hence, the present method facilitates the desired reliable determination of the change in the refractive error of the eye with a high repeatability of the measurement results and therefore typically allows a more reliable classification of the advance of a refractive error and more reliable statements about the success of an intervention for reducing the advance of the refractive error.

In a further aspect, the present disclosure relates to a computer program for determining a refractive error of an eye of a user, wherein the computer program is configured to determine the refractive error of the eye of the user in accordance with the method, described herein, for determining a refractive error of an eye of the user.

The method proposed herein for determining a change in a refractive error of an eye of a user is also suitable for use in a method for producing a spectacle lens for the eye of the relevant user. Pursuant to the standard DIN EN ISO 13666: 2013-10, sections 8.1.1 and 8.1.2, a "spectacle lens" is understood to mean an ophthalmic lens which, within the scope of the present disclosure, should serve to correct a refractive error of the eye, with the ophthalmic lens being worn in front of the eye of the user but not in contact with the eye. The term "a pair of spectacles" denotes any element which comprises two individual spectacle lenses and a spectacle frame, the spectacle lens being provided for insertion into a spectacle frame that is selected by a wearer of the pair of spectacles. In particular, from a determination of the change in the refractive error occurring for the user, it is possible to ascertain a spherocylindrical lens which is used as a spectacle lens to compensate the refractive error occurring as defocusing of the eye, in such a way that an image quality that is as optimal as possible can be obtained for the user.

In a further aspect, the present disclosure therefore relates to a method for producing a spectacle lens, wherein the spectacle lenses are produced by processing a spectacle lens blank, wherein the spectacle lens blank is processed on the basis of correction data and centration data, wherein the centration data comprise instructions for positioning the spectacle lens in front of the eye of a user for the purposes of compensating the refractive error of the eye of the user, wherein a change in the refractive error of the eye of the user is determined in accordance with the method, described herein, for determining a change in a refractive error of an eye of a user. The method for producing a spectacle lens is used, in particular, if the change in the refractive error of the eye of the user reaches or exceeds a threshold, typically selected from an interval from 0.25 dpt to 1.5 dpt, in particular 0.25 dpt; 0.5 dpt; 0.75 dpt; 1 dpt; 1.25 dpt or 1.5 dpt.

In a further aspect, the present disclosure relates to an apparatus for determining the change in the refractive error of the eye of the user, the eye of the user having a choroid. According to the present disclosure, the apparatus comprises:

a measuring device for capturing a layer thickness of the choroid of the eye of the user; and an evaluation device for ascertaining values for the layer thickness of the choroid of the eye over at least two regions of the retina of the eye, wherein the evaluation device is furthermore configured to determine a value for the change in the refractive error of the eye only from at least two values for the layer thickness of the choroid, wherein the values for the layer thickness of the choroid are each ascertained at different times for the at least one region of the choroid, wherein the at least one region of the choroid is selected from a nasal perifoveal region or a nasal parafoveal region of the choroid.

For ascertaining values for the layer thickness of the choroid of the eye and for determining the value for the change in the refractive error of the eye, in particular, it is possible to use an automated software, typically in the evaluation device. Alternatives are a semi-automated evaluation with a manual correction by an examiner or a completely manual evaluation by the examiner by means of determining boundaries between the retinal pigment epithelium of the retina and the choroid and between the choroid and the sclera. To this end, use can be made of known software which carries out a segmentation of each scanned image of an OCT on the basis of brightness differences between adjacent pixels on the basis of a so-called "graph search methodology." It is also possible, as a matter of principle, to apply algorithms from the fields of machine vision, machine learning or artificial intelligence, in particular for segmenting the choroid and for capturing lengths, areas or volumes.

The evaluation device can be any desired device that is configured to receive, process and output data. Typically, this can be an electronically or optoelectronically controllable measuring unit which may be equipped with, in particular, a computer, microcomputer or programmable chip, e.g., an application-specific integrated circuit (ASIC) or an FPGA (field-programmable gate array), wherein the measuring device can access one or more computer programs, which may be configured to carry out the methods described herein. Alternatively, the evaluation device can be comprised by a mobile communications appliance, in particular a smartphone or a tablet. However, other configurations of the evaluation device are possible, for example an integration of the evaluation device in the aforementioned measuring device.

For definitions and optional configurations of the computer program and the apparatus for determining a change in a refractive error of an eye of a user, reference is made to the description, either above or below, of the method for determining a refractive error of an eye of a user.

In summary, in the context of the present disclosure, the following exemplary embodiments are particularly typical:

Exemplary embodiment 1: A method for determining a change in a refractive error of an eye of a user, the eye of the user having a choroid, wherein the method comprises the steps of:
a) ascertaining at least one value for a layer thickness of the choroid of the eye of the user over at least one region of the choroid; and
b) determining a value for the change in the refractive error of the eye only from at least two values for the layer thickness of the choroid which were each captured at different times for the at least one region of the choroid, wherein the at least one region of the choroid is selected from a nasal perifoveal region or a nasal parafoveal region of the choroid.

Exemplary embodiment 2: The method according to the preceding exemplary embodiment, wherein the at least one region of the choroid is selected from the nasal perifoveal region of the choroid.

Exemplary embodiment 3: The method according to any one of the preceding exemplary embodiments, wherein a value for an average layer thickness of the choroid is ascertained over the at least one region.

Exemplary embodiment 4: The method according to the preceding exemplary embodiment, wherein the average layer thickness of the choroid is selected from a mean, typically an arithmetic mean or a geometric mean, a median or a representative value for the layer thickness of the choroid over the at least one region.

Exemplary embodiment 5: The method according to any one of the preceding exemplary embodiments, wherein a partial field is selected from the nasal perifoveal region of the choroid, the field comprising an outer quadrant of an annular space with an inner diameter and an outer diameter centered around a foveal region.

Exemplary embodiment 6: Method according to the preceding exemplary embodiment, wherein the inner diameter is selected from a value of 2 mm to 4.5 mm, typically 2.5 mm to 4 mm, in particular 3 mm.

Exemplary embodiment 7: Method according to any one of the two preceding exemplary embodiments, wherein the outer diameter is selected from a value of 5 mm to 20 mm, typically 5 mm to 12 mm, in particular 6 mm.

Exemplary embodiment 8: The method according to any one of the three preceding embodiments, wherein the partial field corresponds to the nasal perifoveal region.

Exemplary embodiment 9: The method according to any one of the four preceding exemplary embodiments, wherein the partial field corresponds to a region 7 or a region 9 in an ETDRS grid.

Exemplary embodiment 10: The method according to any one of the preceding exemplary embodiments, wherein the values for the layer thickness of the choroid are ascertained by means of performing image processing on a spatially resolved recording of the eye.

Exemplary embodiment 11: The method according to any one of the preceding exemplary embodiments, wherein the values for the layer thickness of the choroid are ascertained by means of an algorithm selected from at least one of the fields of machine vision, machine learning or artificial intelligence.

Exemplary embodiment 12: The method according to any one of the preceding exemplary embodiments, wherein a method selected from an optical method, an acoustic method or a photoacoustic method is used to capture the layer thickness of the choroid.

Exemplary embodiment 13: The method according to the preceding exemplary embodiment, wherein the optical method is selected from a method for optical coherence tomography or an adaptive optical method.

Exemplary embodiment 14: The method according to the preceding exemplary embodiment, wherein the optical coherence tomography method is selected from a Fourier domain OCT, a swept source OCT or a time domain OCT, with the Fourier domain OCT and the swept source OCT being particularly typical.

Exemplary embodiment 15: The method according to the preceding Exemplary embodiment, wherein the Fourier domain OCT comprises a spectral domain OCT.

Exemplary embodiment 16: The method according to any one of the three preceding exemplary embodiments, wherein the adaptive optical method is selected from a method for determining an optical transmission of the choroid or a method for determining an optical reflectivity of the choroid.

Exemplary embodiment 17: A computer program for determining a change in a refractive error of an eye of a user, wherein the computer program is configured to carry out the method steps according to any one of the preceding embodiments.

Exemplary embodiment 18: An apparatus for determining a change in a refractive error of an eye of a user, wherein the apparatus comprises:
a measuring device for capturing a layer thickness of the choroid of the eye of the user; and
an evaluation device for evaluating values for the layer thickness of the choroid of the eye over at least one region of the choroid, wherein the evaluation device is furthermore configured to determine a value for the change in the refractive error of the eye only from at least two values for the layer thickness of the choroid, wherein the values for the layer thickness of the choroid are each ascertained at different times for the at least one region of the choroid, wherein the at least one region of the choroid is selected from a nasal perifoveal region or a nasal parafoveal region of the choroid.

Exemplary embodiment 19: The apparatus according to the preceding exemplary embodiment, wherein the at least one region of the choroid is selected from the nasal perifoveal region of the choroid.

Exemplary embodiment 20: The apparatus according to any one of the two preceding exemplary embodiments, wherein the evaluation device is furthermore configured to ascertain a value for an average layer thickness of the choroid over the at least one region.

Exemplary embodimet 21: The apparatus according to the preceding exemplary embodiment, wherein the evaluation device is furthermore configured to select the average layer thickness of the choroid from a mean, typically an arithmetic mean or a geometric mean, a median or a representative value for the layer thickness of the choroid over the at least one region.

Exemplary embodiment 22: The apparatus according to any one of the four preceding exemplary embodiments, wherein the evaluation device is furthermore configured to select a partial field from the nasal perifoveal region of the choroid, the field comprising an outer quadrant of an annular space with an inner diameter and an outer diameter centered around a foveal region.

Exemplary embodiment 23: The apparatus according to the preceding exemplary embodiment, wherein the evaluation device is furthermore configured to select the inner diameter from a value of 2.5 mm to 4 mm, typically 3 mm.

Exemplary embodiment 24: The apparatus according to any one of the two preceding exemplary embodiments, wherein the evaluation device is furthermore configured to select the outer diameter from a value of 5 mm to 8 mm, typically 6 mm.

Exemplary embodiment 25: The apparatus according to any one of the three preceding exemplary embodiments, wherein the partial field corresponds to the nasal perifoveal region.

Exemplary embodiment 26: The apparatus according to any one of the four preceding exemplary embodiments, wherein the partial field corresponds to a region 7 or a region 9 in an ETDRS grid.

Exemplary embodiment 27: The apparatus according to any one of preceding exemplary embodiments 18 to 26, wherein the evaluation device is furthermore configured to ascertain values for the layer thickness of the choroid by means of performing image processing on a spatially resolved recording of the eye.

Exemplary embodiment 28: The apparatus according to any one of preceding exemplary embodiments 18 to 27, wherein the evaluation device is furthermore configured to use an algorithm selected from at least one of the fields of machine vision, machine learning or artificial intelligence to ascertain the values for the layer thickness of the choroid.

Exemplary embodiment 29: The apparatus according to any one of the preceding exemplary embodiments 18 to 28, wherein the measuring device is selected from an optical measuring device, an acoustic measuring device or a photoacoustic measuring device.

Exemplary embodiment 30: The apparatus according to the preceding exemplary embodiment, wherein the optical measuring device is selected from a device for optical coherence tomography or a device for carrying out an adaptive optical method.

Exemplary embodiment 31: The apparatus according to the preceding exemplary embodiment, wherein the device for optical coherence tomography is configured to carry out a Fourier domain OCT, a swept source OCT or a time domain OCT, with the Fourier domain OCT and the swept source OCT being particularly typical.

Exemplary embodiment 32: The apparatus according to the preceding exemplary embodiment, wherein the Fourier domain OCT comprises a spectral domain OCT.

Exemplary embodiment 33: The apparatus according to any one of the three preceding exemplary embodiments, wherein the device for carrying out the adaptive optical method is configured to carry out a method for determining an optical transmission of the choroid or a method for determining an optical reflectivity of the choroid.

Exemplary embodiment 34: The apparatus according to any one of the sixteen preceding exemplary embodiments, wherein the apparatus has a housing, into which the measuring device and evaluation device have been introduced.

BRIEF DESCRIPTION OF THE DRAWINGS

The disclosure will now be described with reference to the drawings wherein.

DESCRIPTION OF EXEMPLARY EMBODIMENTS

Figure 1:
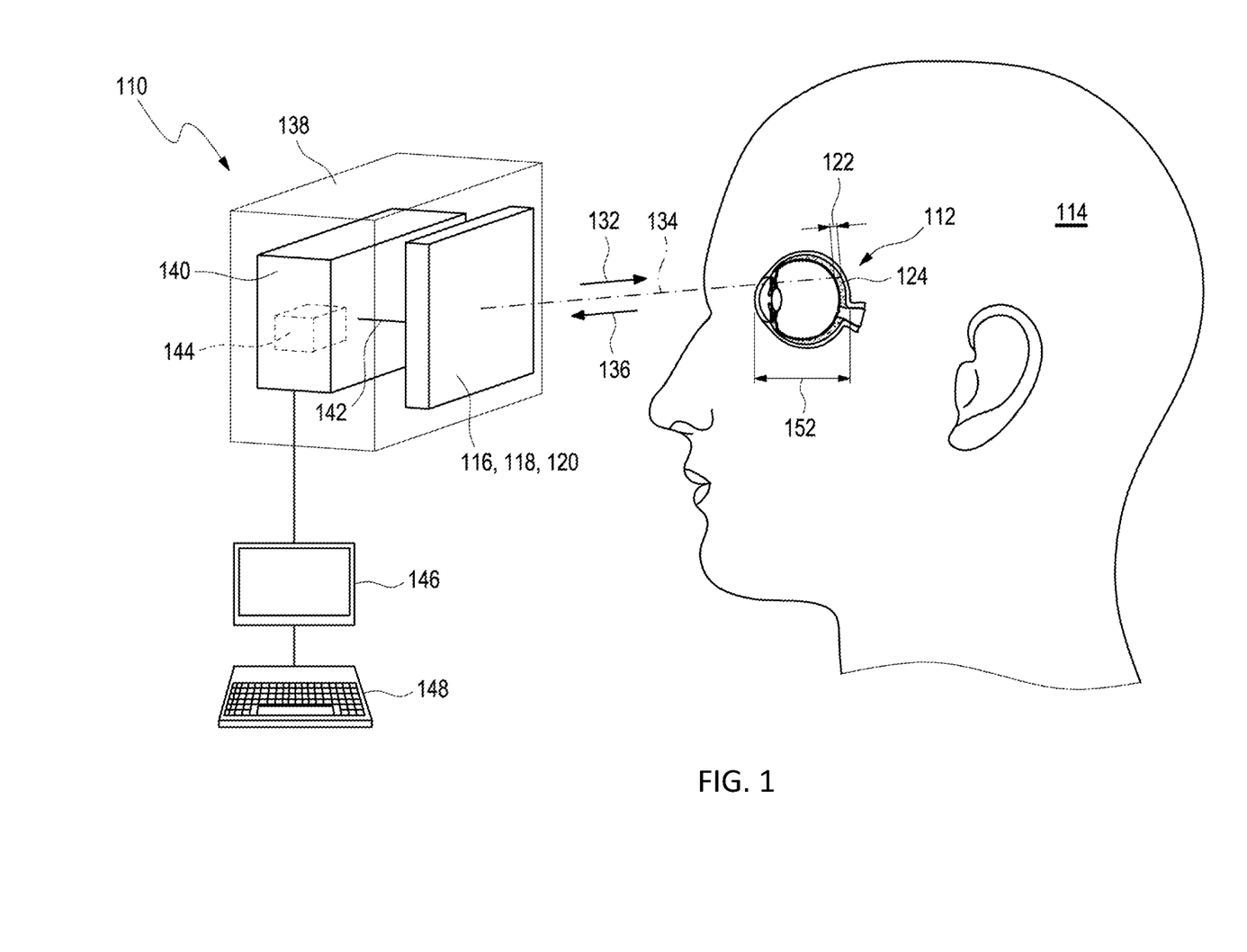
FIG. 1 shows an exemplary embodiment of an apparatus for determining a change in a refractive error of an eye of a user.
Figure 2:
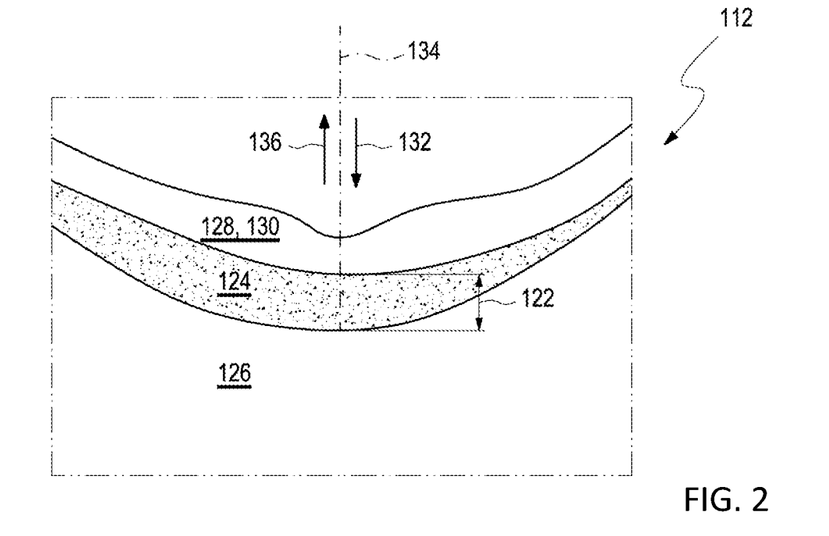
FIG. 2 shows a schematic illustration of a relative position of the choroid between the sclera and retina.

FIG. 1 schematically shows an exemplary embodiment of an apparatus 110 for determining a change in a refractive error of an eye 112 of a user 114. The apparatus 110 comprises a measuring device 116, typically an optical measuring device 118, in particular a device 120 for optical coherence tomography, which is configured to capture a layer thickness 122 of the choroid 124 of the eye 112 of the user 114. However, other types of measuring devices, in particular acoustic or photoacoustic measuring devices, are conceivable. As illustrated schematically in FIG. 2, the choroid (choroidea) 124 represents an intermediate layer which, on the side of the eye 112 distant from the entry of light, is arranged between the sclera 126 and retina 128, in particular between the sclera 126 and the retinal pigment epithelium 130.

The device 120 for optical coherence tomography facilitates an imaging method for generating a 2- or 3-dimensional recording of biological tissue, which in this case comprises the choroid 124, and the sclera 126 and retinal pigment epithelium 130 adjoining the choroid in the eye 112, wherein a resolution in the micrometer range can typically be obtained. To generate the desired recording, light 132 with a temporally short coherence length from a radiation source is split into two parts in a beam splitter, wherein the first part of the light impinges on the tissue along an optical axis 134, wherein a second part of the light is guided over a reference path, and wherein the light 136 reflected by the tissue is made to interfere with the reference light guided over the reference path in order to generate an interference signal. From the interference signal, it is possible initially to only distinguish structures in the tissue along the optical axis 134; however, the desired 2- or 3-dimensional recording of the tissue or a section thereof can be generated by way of a lateral scanning by means of a change in the optical axis 134 over the tissue.

In the present exemplary embodiment, the method for optical coherence tomography can typically be selected from a Fourier domain OCT, in particular a spectral domain OCT or a swept source OCT. Alternatively, a time domain OCT is likewise conceivable. A further alternative configuration can comprise a device for carrying out an adaptive optical method (not illustrated), which is configured to carry out an adaptive optical method, in particular a method for determining an optical transmission or reflectivity of the choroid 124.

As illustrated schematically in FIG. 1, the apparatus 110 can further have a housing 138, which may comprise an evaluation device 140 in addition to the measuring device 116. As an alternative or in addition thereto, the evaluation device 140 may, however, also be attached outside of the housing 138, wherein a wired or wireless connection 142 may be present between the measuring device 116 and the evaluation device 140. The evaluation device 140 can be equipped with a processor 144, which may be provided to carry out one or more algorithms. Furthermore, provision can be made of a monitor 146 for displaying values and a keyboard 148 for entering values or commands. Further types of the embodiment of the apparatus 110, in particular the evaluation device 140, are however also possible.

The evaluation device 140 is configured to ascertain values for the layer thickness 122 of the choroid 124 of the eye 112 over at least one region 150 of the choroid. To this end, the evaluation device 140 can receive variables captured by measurement, which variables are transmitted from the measuring device 116 to the evaluation device 140 via the connection 142, wherein the layer thickness 122 of the choroid 124 of the eye 112 can be derived from the variables captured by measurement.

According to the present disclosure, the evaluation device is furthermore configured to determine a value for the change in the refractive error of the eye 112 only from at least two values for the layer thickness 122 of the choroid 124, wherein the two values for the layer thickness 122 of the choroid 124 are respectively ascertained at different times for the at least one region 150 of the choroid. The at least one region 150 of the choroid 124 in this case denotes a section of the choroid 124 which can typically be selected in relation to a point of the retina 128 adjoining the section. In this case, a value for an average layer thickness 122 of the choroid 124 can typically be ascertained for the at least one region 150 of the choroid 124. However, other types of values are possible.

Typically, a first value for the layer thickness 122 of the choroid 124 is ascertained at a first time and a second value for the layer thickness 122 of the choroid 124 is ascertained at a second time, wherein the desired value for the change in the refractive error of the eye 112 of the user 114 can be ascertained from relating the first value and the second value to one another. To this end, it is possible to estimate a value for a change in a length 152 of the eyeball of the user 114, for example from the change in the layer thickness 122 which can be ascertained from the difference between the first value for the layer thickness 122 and the second value for the layer thickness 122. Using the rule of thumb set forth at the outset, according to which an increase in the length 152 of the eyeball of the user 114 of approximately 1 mm leads to a refractive error of approximately 3 dpt, it is consequently possible to deduce the change in the refractive error of the eye 112 of the user 114.

Figure 3:
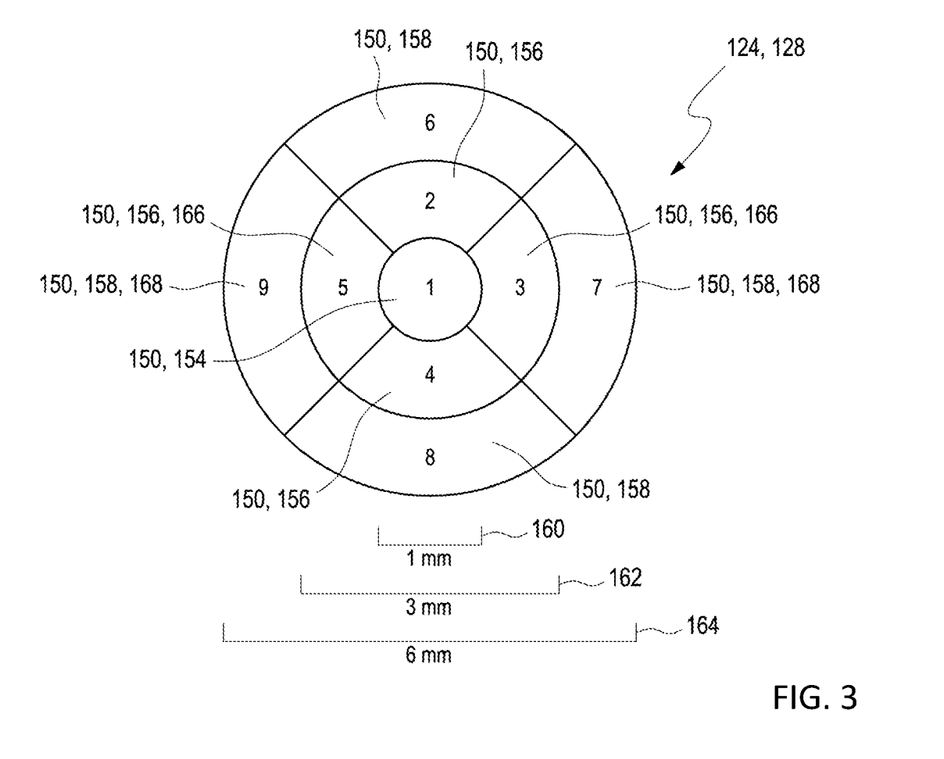
FIG. 3 shows a schematic illustration of a subdivision of the retina into various regions.

FIG. 3 shows the various regions 150 of a so-called "ETDRS grid" of the retina 128, which are provided with numbers "1" to "9". Here, a subfoveal region 154 with the number "1" and parafoveal regions 156 with the numbers "2", "3", "4" and "5" surrounding the subfoveal region 154 are distinguished from the perifoveal regions 158 with the numbers "6", "7", "8" and "9" surrounding the parafoveal regions 156. In a particularly typical configuration, an area of the retina 128 and hence of the choroid 124 adjacent thereto can be split into a subfoveal region 154, parafoveal regions 156 or inner regions surrounding the subfoveal region and perifoveal regions 158 or outer regions surrounding the parafoveal regions. Here, the subfoveal region 154 can typically have a diameter 160 ranging from 0.5 mm to 1.5 mm, typically 1 mm, corresponding to an angle of 3.33°, while the parafoveal regions 156 can extend from touching the latter to an inner diameter 162 and the adjoining perifoveal regions 158 can extend to an outer diameter 164, wherein the inner diameter 162 can typically be selected from a value from 2.5 mm to 4.5 mm, typically 2.5 mm to 4 mm, in particular 3 mm, i.e., corresponding to an angle of 10°, and the outer diameter 164 can typically be selected from a value of 5 mm to 20 mm, typically 5 mm to 12 mm, in particular 6 mm, i.e., corresponding to an angle of 20°. However, other values of the diameters 160, 162, 164 specified here are conceivable.

According to the present disclosure, the at least one region 150 of the choroid 124 which is used to determine the change in the refractive error of the eye 112 of the user 114 is selected from a nasal perifoveal region 168 or a nasal parafoveal region 166 of the choroid 124. While known methods for determining the change in the layer thickness of the choroid evaluate possible changes in the layer thickness 122 of the choroid 124 predominantly in the subfoveal region 154 of the retina 128, it could surprisingly be verified experimentally that a reproducibility of the evaluation is significantly better in the nasal perifoveal region 168 and in the nasal parafoveal region 166, i.e., regions "3" and "7" for the right eye and regions "5" and "9" for the left eye in the ETDRS grid, in particular in the nasal perifoveal region 168, i.e., the region "7" for the right eye and the region "9" for the left eye in the ETDRS grid, than in the subfoveal region 154, in the remaining, i.e., non-nasal, parafoveal regions, i.e., the regions "2" and "4" in the ETDRS grid, and in the remaining, i.e., non-nasal, perifoveal regions, i.e., the regions "6" and "8" in the ETDRS grid.

Examinations using the spectral domain OCT as a measuring method for capturing the layer thickness 122 of the choroid 124 have shown that the best reproducibility occurs predominantly in the nasal parafoveal region 166 and in the nasal perifoveal region 168, in particular in the nasal perifoveal region 168. Table 1 comprises measurement values for the reproducibility of measurements for capturing the layer thickness 122 of the choroid 124, listed according to the individual regions 150 of the choroid 124:

TABLE 1

| Region 150 of the choroid 124 | Reproducibility |
|---|---|
| Subfoveal region 154 | >40 μm, on average 60 μm |
| All parafoveal regions 156 | >20 μm, on average 30 μm |
| All perifoveal regions 158 | >15 μm, on average 30 μm |
| Nasal parafoveal region 166 | >15 μm, on average 25 μm |
| Nasal perifoveal region 168 | >10 μm, on average 20 μm |

Consequently, the nasal perifoveal region 168 offers the most accurate reproducibility within the choroid. In principle, it was found, as verified by the values listed in table 1, that the reproducibility in each region 150 of the choroid 124 improves the more the relevant region 150 is arranged away from the subfoveal region 154 and arranged in the nasal direction. A possible explanation offered for this could lie in a reduction in the layer thickness 122 of the choroid 124 in the regions 150 that are further away from the subfoveal region 154 and in the nasal direction.

Figure 4:
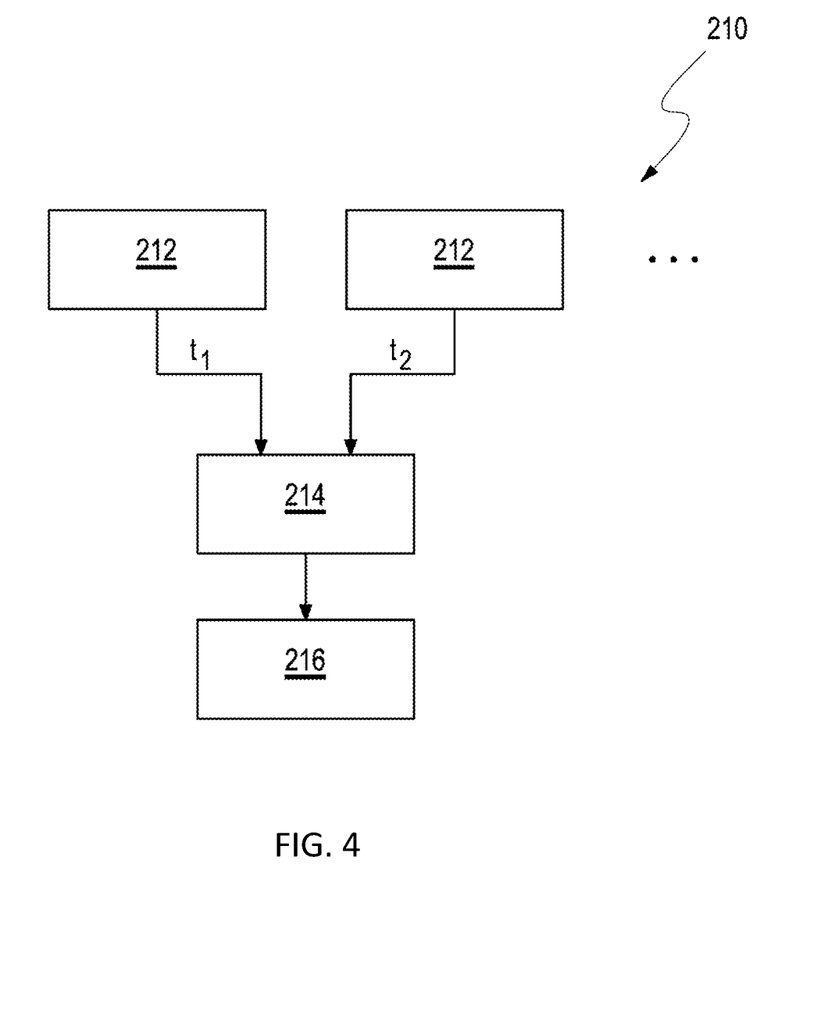
FIG. 4 shows a flowchart of the method according to the disclosure for determining the change in the refractive error of the eye of the user.

FIG. 4 schematically shows a flowchart of a typical exemplary embodiment of a method 210 according to the disclosure for determining the change of the refractive error of the eye 112 of the user 114.

In an ascertainment step 212 there is, as per step a), the ascertainment of at least one value for the layer thickness 122 of the choroid 124 of the eye 112 of the user 114 over the at least one region 150 of the choroid 124.

In a determination step 214 there is, as per step b), the determination of the value 216 for the change in the refractive error of the eye 112 of the user 114 only from at least two values for the layer thickness 122 of the choroid 124 which were each ascertained at different times $t_1, t_2, \ldots$ for the at least one region 150 of the choroid 124, wherein the at least one region 150 of the choroid 124 is selected from the nasal perifoveal region 168 or the nasal parafoveal region 166 of the choroid 124.

Hence, the present method 210 facilitates the desired reliable determination of the change in the refractive error of the eye 112 of the user 114 with a high repeatability of the measurement results and therefore typically allows a more reliable classification of the advance of a refractive error and more reliable statements about the success of an intervention for reducing the advance of the refractive error.

The foregoing description of the exemplary embodiments of the disclosure illustrates and describes the present invention. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art. The exemplary embodiments are illustrated schematically in the drawings. In the drawings, identical reference numerals in the individual figures designate identical or functionally identical elements or elements corresponding to one another with regard to their functions.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

LIST OF REFERENCE SIGNS 110 apparatus
112 eye
114 user
116 measuring device
118 optical measuring device
120 device for optical coherence tomography
122 layer thickness
124 choroid (choroidea)
126 sclera
128 retina
130 retinal pigment epithelium
132 light
134 optical axis
136 reflected light
138 housing
140 evaluation device
142 connection
144 processor
146 monitor
148 keyboard
150 region
152 length of the eyeball
154 subfoveal region
156 parafoveal region
158 perifoveal region
160 diameter
162 inner diameter
164 outer diameter
166 nasal parafoveal region
168 nasal perifoveal region
210 method for determining a change in a refractive error of an eye of a user
212 ascertainment step
214 determination step
216 value of the change in the refractive error of the eye of the user

The invention claimed is:

1. A method for determining a change in a refractive error of an eye of a user, the eye of the user having a choroid, the method comprising:
   ascertaining at least one first value for a layer thickness of the choroid of the eye of the user over at least one region of the choroid;
   ascertaining at least one second value for the layer thickness of the choroid of the eye of the user over the at least one region of the choroid; and
   determining a change in the refractive error of the eye, wherein the change in the refractive error of the eye is determined only from a difference of the at least one first and second values for the layer thickness of the choroid which were each ascertained at different times for the at least one region of the choroid, and
   wherein the at least one region is selected from a nasal perifoveal region or a nasal parafoveal region, which offer the most accurate measurement reproducibility.

2. The method as claimed in claim 1, wherein the at least one region is the nasal perifoveal region.

3. The method as claimed in claim 1, wherein an average layer thickness of the choroid is ascertained in the at least one region.

4. The method as claimed in claim 1, wherein a partial field is selected from the nasal perifoveal region of the choroid, and wherein the partial field includes an outer quadrant of an annular space with an inner diameter and an outer diameter centered around a foveal region.

5. The method as claimed in claim 1, wherein the values for the layer thickness of the choroid are ascertained by performing image processing on a spatially resolved recording of the eye.

6. The method as claimed in claim 1, wherein the layer thickness of the choroid is captured with an optical method, an acoustic method, or a photoacoustic method.

7. The method as claimed in claim 6, wherein the optical method is selected from a method for optical coherence tomography or an adaptive optical method.

8. The method as claimed in claim 7, wherein the optical coherence tomography method is selected from a Fourier domain OCT, a swept source OCT or a time domain OCT, or wherein the adaptive optical method is selected from a method for determining an optical transmission or a method for determining an optical reflectivity.

9. A non-transitory computer storage medium storing a computer program for determining a change in a refractive error of an eye of a user, the eye of the user having a choroid, the computer program being configured to:
ascertain at least one first value for a layer thickness of the choroid of the eye of the user over at least one region of the choroid;
ascertain at least one second value for the layer thickness of the choroid of the eye of the user over the least one region of the choroid at a different time; and
determine a change in the refractive error of the eye,
wherein the change in the refractive error of the eye is determined only from the difference of the at least one first and second values for the layer thickness of the choroid which were each ascertained at different times for the at least one region of the choroid, and
wherein the at least one region is selected from a nasal perifoveal region or a nasal parafoveal region, which offer the most accurate measurement reproducibility.

10. The non-transitory computer storage medium as claimed in claim 9, wherein the computer program is further configured to capture a layer thickness of the choroid with a measuring device selected from an optical measuring device, an acoustic measuring device, and a photoacoustic measuring device.

11. The non-transitory computer storage medium as claimed in claim 10, wherein the optical measuring device is selected from a device for optical coherence tomography or a device for carrying out an adaptive optical method.

12. The non-transitory computer storage medium as claimed in claim 11, wherein the device for optical coherence tomography is configured to carry out a Fourier domain OCT, a swept source OCT or a time domain OCT or wherein the device for carrying out the adaptive optical method is configured to carry out determination of an optical transmission or an optical reflectivity.

13. An apparatus for determining a change in a refractive error of an eye of a user, the eye of the user having a choroid, the apparatus comprising:
a measuring device configured to capture a layer thickness of the choroid of the eye of the user; and
an evaluation device configured to ascertain values for the layer thickness of the choroid over at least one region of the choroid,
wherein the evaluation device is further configured to:
determine a value for the change in the refractive error of the eye only from a difference of at least first and second values for the layer thickness of the choroid, wherein the at least one first value for the layer thickness of the choroid and the at least one second value for the layer thickness of the choroid are each ascertained at different times for the at least one region of the choroid, and wherein the at least one region is selected from a nasal perifoveal region or a nasal parafoveal region, which offer the most accurate measurement reproducibility.

14. The apparatus as claimed in claim 13, wherein the evaluation device is configured to ascertain a value for an average layer thickness of the choroid over the at least one region.

15. The apparatus as claimed in claim 13, wherein the evaluation device is a configured to select a partial field from the nasal perifoveal region of the choroid, and wherein the partial field includes an outer quadrant of an annular space with an inner diameter and an outer diameter centered around a foveal region.

16. The apparatus as claimed in claim 13, wherein the measuring device configured to capture a layer thickness of the choroid is selected from an optical measuring device, an acoustic measuring device, and a photoacoustic measuring device.

17. The apparatus as claimed in claim 13, wherein the optical measuring device is selected from a device for optical coherence tomography or a device for carrying out an adaptive optical method.

18. The apparatus as claimed in claim 13, wherein the device for optical coherence tomography is configured to carry out a Fourier domain OCT, a swept source OCT or a time domain OCT or wherein the device for carrying out the adaptive optical method is configured to carry out determination of an optical transmission or an optical reflectivity.

* * * * *

UNITED STATES PATENT AND TRADEMARK OFFICE
CERTIFICATE OF CORRECTION

PATENT NO. : 11,185,223 B2  
APPLICATION NO. : 17/183573  
DATED : November 30, 2021  
INVENTOR(S) : Ohlendorf et al.

Page 1 of 1

It is certified that error appears in the above-identified patent and that said Letters Patent is hereby corrected as shown below:

In the Specification

Column 11, Line 29, change "Exemplary embodimet" to -- Exemplary embodiment --.

Signed and Sealed this  
First Day of March, 2022

Drew Hirshfeld  
*Performing the Functions and Duties of the*  
*Under Secretary of Commerce for Intellectual Property and*  
*Director of the United States Patent and Trademark Office*